United States Patent
Marini

(10) Patent No.: US 8,318,678 B2
(45) Date of Patent: Nov. 27, 2012

(54) COSMETIC COMPOSITIONS

(75) Inventor: Jan L. Marini, San Jose, CA (US)

(73) Assignee: Jan Marini Skin Research, San Jose, CA (US)

( * ) Notice: Subject to any disclaimer, the term of this patent is extended or adjusted under 35 U.S.C. 154(b) by 759 days.

(21) Appl. No.: 12/130,891

(22) Filed: May 30, 2008

(65) Prior Publication Data

US 2010/0029574 A1    Feb. 4, 2010

(51) Int. Cl.
*A61K 8/64* (2006.01)
*A61K 38/07* (2006.01)
*A61K 38/08* (2006.01)

(52) U.S. Cl. .................. 514/20.7; 514/21.8; 514/21.9; 514/20.8

(58) Field of Classification Search .................. None
See application file for complete search history.

(56) References Cited

U.S. PATENT DOCUMENTS

| 5,789,542 | A | 8/1998 | McLaughlin et al. |
| 5,955,343 | A | 9/1999 | Holmes et al. |
| 2003/0147823 | A1 | 8/2003 | Woodward et al. |
| 2004/0052760 | A1 | 3/2004 | Michelet et al. |
| 2007/0020220 | A1 | 1/2007 | Osborne |
| 2007/0166267 | A1 | 7/2007 | Majewski et al. |

FOREIGN PATENT DOCUMENTS

| WO | 2007/143006 | 12/2007 |
| WO | 2009/148947 | 12/2009 |
| WO | WO 2009/148947 A1 * | 12/2009 |

OTHER PUBLICATIONS http://www.skin-etc.com/janmaageiney.html, "Marini Lash Eyelash Conditioner", May 4, 2007.*
Wolf, Ronni; et al., Prostaglandin analogs for hair growth: Great expectations, Dermatology Online Journal, 2003, 9(3)7, downloaded Sep. 10, 2008.
Sasaki; et al., "Influence of prostagladin F2alpha and its analogues on hair regrowth and follicular melanogenesis in a murine model", Experimental Dermatology, 2005, 14:323-328.

* cited by examiner

*Primary Examiner* — Christina Bradley
(74) *Attorney, Agent, or Firm* — Bozicevic, Field & Francis LLP; Pamela J. Sherwood

(57) ABSTRACT

The present invention generally features novel cosmetic skin and hair care compositions for enhancing the appearance of eyelashes and eyebrows. Specifically, the topical skin and hair care compositions of the invention contain a concentration of at least one of pentapeptide-17 tetrapeptide-12 that provide for thicker, longer and more voluminous appearing eyelashes and eyebrows. The cosmetic formulations of the invention may further include cosmetically acceptable vehicle(s) and/or other skin and hair conditioning agents.

1 Claim, No Drawings

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)
<223> OTHER INFORMATION: acylated amino acid

<400> SEQUENCE: 1

Lys Leu Ala Lys Lys
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic oligopeptide
<220> FEATURE:
<221> NAME/KEY: MOD_RES
<222> LOCATION: 1
<223> OTHER INFORMATION: acylated amino acid

<400> SEQUENCE: 2

Lys Ala Lys Ala
1
```

COSMETIC COMPOSITIONS

BACKGROUND OF THE INVENTION

Cosmetics are often used to highlight and enhance a person's natural beauty. Various trends in fashion encourage the use of a variety of beauty enhancing products and practices. The use of makeup is one such practice commonly engaged in for the purpose of maintaining a healthy, vibrant and youthful appearance. An assortment of makeup products to be applied to the face and hair are sold worldwide, these include lipstick, rouge, eye shadow, mascara, facial powders, creams, shampoos, conditioners and the like, all of which are makeup and/or cosmetic items well known in the art.

Most of the products currently sold as cosmetics have only a temporary effect. They are meant to be applied and then washed off at a later time. Accordingly, although they are useful in improving the appearance, their effectiveness is severely limited by the short duration of their use. Another limitation is that the addition of a cosmetic, if not applied properly, can give a user an unnatural and/or artificial appearance. Current trends in fashion promote a more natural, as opposed to an artificial, appearance. As a result, appearance enhancing products that are designed to promote the body's natural ability to replenish and appear healthier are highly sought after.

One trend currently being followed is to enhance the appearance of the eye-lashes and eye-brows. It is commonly thought that having eyelashes that appear thicker, longer and give a more voluminous feeling to the eyelashes is aesthetically pleasing. Accordingly, eye care products, such as eye-liners and mascaras, are being marketed for their abilities to give a thicker and longer appearance to the eyelashes and a more voluminous appearance to the eyebrows. However, in order to achieve these effects many mascara products typically incorporate high levels of waxes and film forming polymers into the formulation. This generally makes the washing of the mascara off the eyelashes difficult, which in turn can cause damage to the actual eyelashes. Attempts to solve this problem by use of thin moisturizing mascaras have been unsuccessful as such products are usually not thickening or lengthening in effect and do not wear well because they smudge and smear easily.

Other attempts to give the eyelashes a thicker, longer and more voluminous appearance without the problems associated with mascara (e.g., smudging and smearing) include the use of "false eyelashes" as a cosmetic accessory. False eyelash systems and devices, however, are difficult to use, hard to remove and may give the user an artificial, prefabricated look and feel.

There is, therefore, an interest in developing cosmetic compositions that provide a more natural, healthy and vibrant appearance of the eyelashes and eyebrows that are longer lasting, that do not suffer from smudging or smearing, and do not give an artificial appearance when used. The compositions and methods of the present invention meet these and other needs.

RELEVANT LITERATURE

U.S. Patent application 20030147823; U.S. Patent application 20040052760. Wolf et al. (2003) Dermatology Online Journal 9(3):7. Sasaki et al. (2005) Experimental Dermatology 14:323.

SUMMARY OF THE INVENTION

The present invention generally features cosmetic skin and hair care compositions for enhancing the appearance of eyelashes and eyebrows. Specifically, the topical skin and hair care compositions of the invention contain active ingredients that provide for thicker, longer and more voluminous appearing eyelashes and eyebrows. Such ingredients include one or more acylated peptides, e.g. pentapeptide-17 and/or tetrapeptide-12. The cosmetic formulations of the invention may further include herbal extracts, cosmetically acceptable vehicle (s) and/or other skin and hair conditioning agents. Additional agents to enhance skin penetration may be included in the formulation.

DETAILED DESCRIPTION OF THE EMBODIMENTS

Topical compositions are provided for enhancing the appearance of hair. The compositions are administered to the region of skin comprising hair follicles, particularly skin comprising the hair of the eyelashes and eyebrows; and of the scalp. The compositions of the invention provide active ingredients that are specially formulated to enhance the natural appearance of the eyelashes and eyebrows. Of particular interest is the application of the hair care compositions to the eyelashes, eyebrows and/or surrounding skin to give the eyelashes and eyebrows a thicker, longer and more voluminous appearance.

Components of the Cosmetic Compositions

Acylated Peptides. The compositions of the invention comprise at least of one acylated pentapeptide or tetrapeptide, which may be generally referred to herein as peptides, at a concentration of from about 0.001 μg/ml to not more than about 1 μg/ml. Such peptides are acylated, and this comprise at least one lipid moiety, which moiety may be octanoyl, decanoyl, lauroyl, myristoyl, palmitoyl, stearoyl, oleoyl, linoleoyl, arachidonoyl, etc., which increases the hydrophobicity of the peptide. Myristoylated peptides are of particular interest. Peptides may be modified with a single acyl group, or may be provided as a cocktail of different acyl groups. The lipid moiety is usually conjugated to the amino or carboxy terminus of the peptide, usually the carboxy terminus. If unconjugated, the amino terminus may be an amino or an amide group. As used herein, "peptides" refers to both naturally occurring peptides and synthesized peptides.

Peptides of interest include pentapeptide-17, which is a five amino acid peptide having the amino acid sequence SEQ ID NO:1 Ac-KLAKK, where "Ac" refers to an acyl group as described above, e.g. myristoyl, palmitoyl, etc. The peptide may have an amino terminus or an amide group at the terminus.

Another peptide of interest is tetrapeptide-12, which is a four amino acid peptide having the amino acid sequence SEQ ID NO:2 Ac-KAKA, where "Ac" refers to an acyl group. The peptide may have an amino terminus or an amide group at the terminus.

In some embodiments of the invention a combination of tetrapeptide-12 and pentapeptide-17 is used. The ratio of peptides (pentapeptide-17:tetrapeptide-12) on a weight basis is usually from about 10:1 to about 1:10; from about 5:1 to about 1:5; from about 5:1 to about 1:1; from about 5:1 to about 2:1; and in some embodiments is about 4:1; about 5:3; about 5:2; or about 3:1.

The amino acid sequence of pentapeptide-17 or tetrapeptide-12 can be altered in various ways known in the art to generate targeted changes in sequence. Such variants will typically be functionally-preserved variants, which differ in sequence, from the provided peptide but still retain the desired biological activity of enhancing the natural appearance of the eyelashes and eyebrows. Various methods known in the art can be used to generate targeted changes.

The peptides of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. If desired, various groups can be introduced into the protein during synthesis, e.g. amide groups, acyl groups, and the like.

Peptide modifications of interest that do not alter primary sequence include chemical derivatization of proteins, e.g., acetylation or carboxylation. Also included are modifications of glycosylation. Also embraced are sequences that have phosphorylated amino acid residues, e.g. phosphotyrosine, phosphoserine, or phosphothreonine.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al (2000) *J. Biol. Chem.* 275:23783-23789). Analogs of such proteins include those containing residues other than naturally occurring L-amino acids, e.g. D-amino acids or non-naturally occurring synthetic amino acids.

The cosmetic compositions of the present invention are for topical use and are to be applied to the hair and skin of the eyelash and eyebrow regions of the face. The amounts and concentrations of the peptides in the compositions of the invention will vary depending on several different factors, including but not hereby limited to, the pH and condition of the skin; whether the skin is oily, dry, or in-between; and the nature of the interaction between the various other agents to be included in the composition, but should be such to be effective while at the same time reducing the risk of untoward side effects, such as inflammation and the unwanted change in the pigmentation of the hair or eyes. Optimization of the concentration of the active agent(s), suitable for use with different skin types, which are used within the compositions of the invention, can be routinely determined by a skilled worker using well known methods that are commonly practiced within the art.

In general, the subject cosmetic compositions will typically contain at least about 0.001 μg/ml of pentapeptide-17 and/or tetrapeptide-12 as an active ingredient, at least about 0.01 μg/ml, at least about 0.05 μg/ml, at least about 0.1 μg/ml, at least about 0.5 μg/ml, and not more than about 10 μg/ml, usually not more than about 1 μg/ml. The peptides may be provided as a 500 ppm solution, i.e. 0.5 mg/ml, of which from about 0.01 to about 0.5 ml may be diluted into 100 ml, final volume. The peptide agents of the present invention are formulated at an effective concentration within the subject cosmetic compositions, meaning at a concentration that provides the intended benefit when applied topically.

In order to be effective in stimulating hair growth the composition may be formulated in such a way as to enable the active agents to penetrate the skin. Accordingly, the composition may be formulated in conjunction with a skin penetration enhancing agent so as to better enable the active agent to deeply penetrate the epidermis of the skin.

In one embodiment of the invention, the formulation comprises one or more skin penetration enhancing and/or buffering agents. In certain embodiments, a composition of the invention includes as an active agent pentapeptide-17 and/or tetrapeptide-12 in a synergistic combination with at least one skin penetration enhancing agent, and which may also include a suitable buffering agent.

Skin penetration enhancing agents function to increase the penetration of the active agents of the composition. A skin penetration enhancing agent, therefore, may be any factor that increases the penetration of the skin, preferably with minimal disruption to the acidic pH balance of the skin. Preferably, the skin penetration enhancing agent enhances the percutaneous delivery of the active agent into and through the layers of the skin, without providing substantial transdermal transmission of the active agent into the systemic circulation. The permeability enhancing agents of the invention are physio-chemically stable, do not have pharmacological effects, and have at least reduced irritancy or toxicity to the skin. When present in a composition of the invention, the amount of penetration enhancer is typically from about 1% to about 10% by weight of the total composition weight or from about 2% to about 5% by weight. The formulation and use of skin penetration enhancers in topical formulations is set forth generally in: PERCUTANEOUS PENETRATION ENHANCERS (Eric W. Smith & Howard I. Maibach eds. 1995); Ghosh, T. K. et al. 17 PHARM. TECH. 72 (1993); Ghosh, T. K. et al. 17 PHARM. TECH. 62 (1993); and Ghosh, T. K. et al. 17 PHARM. TECH. 68 (1993), all of which are hereby incorporated herein by reference in their entirety.

Suitable skin penetration enhancing agents include those agents that are capable of reducing the resistance of the skin to the active agent and promoting the active agent partitioning from the dosage form. Penetration enhancing agents may function in a variety of ways, including via the elution of the lipid and/or lipoprotein structures of the stratum corneum, by increasing lipid fluidity (e.g., by disrupting the tightly packed lipid chains), or by engaging in various protein interactions that result in a change in protein and/or lipid configuration that creates a passage for the active agent (e.g., pentapeptide-17 and/or tetrapeptide-12). Suitable topical skin permeability enhancing agents can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87, which is hereby incorporated by reference in its entirety.

Accordingly, suitable skin penetration enhancing agents include but are not hereby limited to: sulfoxides, alcohols, polyols, fatty acids, esters, amides, surface active agents (such as pluronics, sulfates, lecithin, docusate sodium, polysorbates), water, and the like. Specifically, skin penetration enhancing agents include but are not hereby limited to dimethyl sulfoxide (DMSO), N-decylmethylsulfoxide, ethanol, phenyl ethanol, propylene glycol, lauric or myristic or palmitic or steric fatty acids, lauric acid, sodium laurate, neodecanoic acid, lauryl lactate, methyl laurate, hexamethylene lauramide, leucinic acid, oleic acid, capric acid, sodium oleate, sodium caprate, dodecyl-amine, cetryl lactate, myristyl lactate, isopropyl palmitate or isopropyl myristate esters, urea and derivatives, dodecyl N,N-dimethylamino acetate, hydroxyethyl lactamide, lecithin, phyophatidylcholine, sefsol-318 (a medium chain glyceride, surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-methyl-2-pyrrolidone, 1-lauryl-2-pyrrolidone, sucrose monooleate, acetone, polyethylene glycol 100-400 MW, dimethylacetamide, dimethylforamide, dimethylisosorbide, sodium bicarbonate, mentane, menthone, menthol, terpinene, D-terpinene, dipentene, N-nonalol, limonene, and various $N_{7-1}$-alkanes in amounts that are safe and effective.

An exemplary vasodilator that finds us in the cosmetic compositions of the present invention is niacinamide (a vitamin $B_3$ compound), which aids in the penetration and uptake of active ingredients. The niacinamide may be used at a concentration of at least about 0.25% to 0.5%, more usually at least about 1%, and not more than about 5%.

The normal pH of the skin of the face is between about 4 and about 6.5, though it varies in people of different skin types. The compositions of the invention, therefore, in certain embodiments, should be formulated in such a manner so as to reduce the effects that the actual application of the composition has on the pH barrier of the skin and/or should be formulated in a manner so as to increase the penetration of the active agent. Accordingly, in certain embodiments the typical pH ranges for the compositions of the invention include a pH of about 3 to about 8, of about 4 to about 7, and more typically about 4.5 to about 6.5 or about 5. The desired pH ranges of the compositions of the invention can be obtained in accordance with practices well known in the art, for instance, by the inclusion of various buffering agents, which should be included in an amount and concentration to optimize the flux of the active agent through the skin surface and into the dermal layer of skin, while minimizing any possibility of skin irritation due to a change in the pH of the skin.

Herbal Extracts

The cosmetic compositions of the invention may comprise one or more herbal extracts, where the extracts are each present at a concentration of from about 0.001%, from about 0.01%, about 0.1, to not more than about 1% or not more than about 2%. Herbal extracts of interest for use in the present formulation include, without limitation, *Cinnamomum zeylanicum* bark extract, *Aesculus hippocastanum* seed extract, and *Camellia sinensis* leaf extract.

White tea (*Camellia sinensis*) is an anti-inflammatory agent. In addition, the topical use of tea extracts may promote the health and quantity of collagen, thereby maintaining a firm and elastic skin. The flavonoids and catechols in tea provide it with vitamin P properties and the tannins in its chemical composition give it astringent properties, whereas the polyphenolic compounds also act as an astringent, but also protect the skin. The Methylxanthines contained in tea also stimulate skin microcirculation and therefore positively influence the tone and health of the skin. Horse chestnut seed (*Aesculus hippocastanum*) may have anti-inflammatory properties for skin. Cinnamon (*Cinnamomum zeylanicum*) may have antimicrobial and antioxidant properties (*Cutaneous and Ocular Toxicology*, March 2007, pages 227-233; and *Letters in Applied Microbiology*, January 2002, pages 27-31).

Lipophilic Agents

Various lipophilic agents may also be included as cosmetic benefit agents of the present invention in amounts that are safe and effective. A lipophilic agent to be added to a composition of the invention may be, for instance, a water-insoluble (hydrophobic) organic material or mixture of materials that are miscible with acylated peptides and are suitable for topical administration and formulated to enhance the penetration of an active agent of the invention. A lipophilic component may be in a range about 15% to about 40% by weight of the total composition weight or about 20% by weight.

Suitable lipophilic components are well known in the art and include, but are not limited to, vegetable, nut, and seed oils, such as almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, crambe oil, wheat germ oil, and cocoa butter; animal oils and fats, such as lanolin, tallow, lard, beef fat, butterfat, mink oil, and fish oils; hydrocarbon and petroleum oils, such as petrolatum, mineral oil, and liquid paraffin. Additional lipophilic components include higher fatty acids such as lauric acid, myristic acid, palmitic acid, stearic acid, behenic acid, oleic acid, 12-hydroxystearic acid, undecylenic acid, tall acid, lanolin fatty acid, isostearic acid, linoleic acid and linolenic acid.

The lipophilic component may also include a suitable stiffening agent such as isopropyl myristate, glycerol monolaurate, glycerol monooleate, glycerol monolinoleate, isopropyl isostearate, isopropyl linoleate, isopropyl myristate/fatty acid monoglyceride combination, isopropyl myristate/ethanol/L-lactic acid combination, isopropyl palmitate, methyl acetate, methyl caprate or methyl laurate.

A composition of the invention may include spironolactone. Spironolactone. (17-hydroxy-7α-mercapto-3-oxo-17α-pregn-4-ene-21-carboxylic acid γ-lactone acetate) is classified as an androgen receptor blocking agent (ARB). Specifically, spironolactone inhibits the effect of aldosterone by competing with it for the binding of the intracellular aldosterone receptor. Effective topical application of spironolactone may be difficult because of its insolubility in water. As such, the cosmetic compositions of the present invention are carefully formulated to provide spironolactone in an active form, thereby maximizing its effectiveness. In some embodiments, additional ingredients of the subject cosmetic compositions will act synergistically with spironolactone. In general, the subject cosmetic compositions may contain at least about 1%, at least about 2.5%, at least about 5%, and usually not more than about 10% (weight/weight) spironolactone as an active ingredient.

The cosmetic compositions of the present invention may also be prepared with microsponges, liposomes, micelles, and microspheres. Microsponges are microscopic, porous spherical sponges that are virtually invisible to the human eye. Generally, they are porous microspheres having a myriad of interconnected voids of particle size range 5-300 μm. Depending upon the size, the total pore length may range up to 10 ft and pore volume may range up to 1 ml/g. Microsponges have the capacity to entrap an active agent and/or other cosmetically suitable compound such as an emollient, surfactant, essential oils, sunscreens and anti-infective, etc. and can be used with the active agent(s) of the invention (e.g., a prostaglandin or an analog thereof) as a topical carrier system. The active agent(s) of the invention can be incorporated in to a microsponge and formulated into creams, lotions and powders.

Microsponges are formulated for prolonged release and can thereby prevent excessive accumulation of ingredients within the epidermis and the dermis, which allows greater penetration of the active agent. Additionally, because of the sustained release, the use of a microsponge as an active agent carrier can significantly reduce the irritation of the active agent without reducing its efficacy. Other forms of microspheres may be incorporated into the present formulations of the invention. For instance, microspheres formed from lipids, typically charged lipids such as phospholipids. Preparation of lipidic microspheres is well known in the art.

Liposomes are microscopic vesicles having a lipid wall comprising a lipid bilayer, and can be used as drug delivery systems herein as well. Generally, liposome formulations are preferred for poorly soluble or insoluble cosmetic agents. Liposomal preparations for use in the instant invention include cationic (positively charged), anionic (negatively charged) and neutral preparations. Cationic liposomes are readily available. For example, N-[1-2,3-dioleyloxy)propyl]-N,N,N-triethylammonium liposomes are commercially available. Anionic and neutral liposomes are commercially and readily available as well, or can be easily prepared using readily available materials. Such materials include phosphatidyl choline, cholesterol, phosphatidyl ethanolamine, dioleoylphosphatidyl choline, dioleoylphosphatidyl glycerol, dioleoylphoshatidyl ethanolamine, among others. These materials can also be mixed with N-[1-2,3-dioleyloxy)propyl]-N,N,N-triethylammonium (DOTMA) in appropriate ratios. Methods for making liposomes using these materials are well known in the art.

Micelles are known in the art and are comprised of surfactant molecules (described in greater detail herein below) arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention by formulation with the active agents and other cosmetically suitable agents of the invention so as to be topically applied to the body surface (e.g., a portion of the face).

A composition of the invention may also contain irritation-mitigating additives to minimize or eliminate the possibility of skin irritation or skin damage that may result from the penetration of the active agent or other components of the formulation. Suitable irritation-mitigating additives include, for example: α-tocopherol; monoamine oxidase inhibitors, particularly phenyl alcohols, such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the formulation at a concentration effective to mitigate irritation or skin damage, typically representing not more than about 20 wt %, more typically not more than about 5 wt %, of the formulation.

Cosmetically Acceptable Vehicle

The compositions of the invention comprise a cosmetically acceptable vehicle to act as a dilutant, dispersant or carrier for an active agent (such as a prostaglandin or analog thereof) of the invention, so as to facilitate its distribution and uptake when the composition is applied to the skin and/or hair or scalp. Vehicles other than or in addition to water can include liquid or solid emollients, solvents, humectants, thickeners and powders.

The cosmetically acceptable vehicle will usually form from 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

A topical cosmetic composition of the invention will typically be formulated as a lotions, which are prepared to be applied to the skin surface without friction, and are typically liquid or semiliquid preparations in which solid particles, including the active agent(s) of the invention, are present in a lipid, alcohol or water base. Lotions are usually suspensions of solids, and typically, for the present purpose, comprise a liquid oily emulsion of the oil-in-water type. Lotions are typical formulations herein for treating the facial and scalp areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are, typically, homogeneous mixtures prepared by dissolving one or more chemical substances (solute) in another liquid such that the molecules of the dissolved substance are dispersed among those of the solvent. The solution may contain other cosmetically acceptable chemicals to buffer, stabilize or preserve the solute. Commonly used examples of solvents used in preparing solutions are ethanol, water, propylene glycol or any other cosmetically acceptable vehicle, as for example, set forth below.

When the compositions of the invention are formulated as an oily solution or gel, the fatty phase may constitute more than 90% of the total weight of the composition.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylatelcaprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct components may also be incorporated into the cosmetic compositions. These ingredients may include coloring agents, opacifiers and perfumes. Specifically, these ingredients may include cosmetically suitable additives such as deionized water, hydrolyzed glycosaminoglycan, sodium hyaluraonate, triethanolamine, propylene glycol, methylparaben, propylparaben, acrylates, C10-C20 alkyl acrylate crosspolymers, C12-C15 alkyl benzoate, panthenol, biotin, sodium chloride, sodium phosphate and the like. Amounts of these other adjunct components may range anywhere from 0.001% up to 20% by weight of the composition. In certain embodiments the compositions of the invention do not include a15-hydroxy-prostaglandinn dehydrogenase inhibitor.

Product Use, Form, and Packaging

In use, a quantity of the composition, for example from about 0.0001 ml to 100 ml, from about 0.001 ml to 10 ml, from about 0.01 ml to about 1 ml, typically about 0.1 ml is applied to a site of interest (i.e., skin or hair of the eyelash, eyebrow, and/or scalp) from a suitable container or applicator and, if necessary, it is then spread over the site using a suitable device, usually a fine brush. The product may be specifically formulated for use as a treatment for a specific area, e.g. the eyelashes, eyebrows, the face, the hair, or the scalp.

The cosmetic composition of the invention can be formulated in any form suitable for application to the site of interest). The composition can be packaged in a suitable container to suit its viscosity and intended use by the consumer. For example, a gel can be packaged in a bottle or a container fitted with a fine brush suitable controlled application to the lash line or eyebrow. The invention accordingly also provides a closed container containing a cosmetically acceptable composition as herein defined and may include a suitable applicator, for instance, a fine brush like applicator that is attached to a lid of the container.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates topical compositions according to the present invention. The compositions can be processed in conventional manner. They are suitable for cosmetic use.

| Eyelash Serum | |
|---|---|
| Deionized Water | qs to 100% |
| Myristoyl Pentapeptide-17 and/or Myristoyl Tetrapeptide-12 (500 ppm) | 0.2% |
| Sodium Hyaluronate (and) Hydrolyzed Glycosaminoglycans | 3.0% |
| Propylene Glycol (and) Diazolidinyl Urea (and) Methylparaben, (and) Propylparaben | 1% |
| C12-C15 Alkyl Benzoate | 0.5% |
| Panthenol, 50% soln. | 0.5% |
| Acrylates/C10-C30 Alkyl Acrylates Crosspolymer | 0.44% |
| Linoleic Acid (and) Linolenic Acid (and) Tocopherol | 0.1% |
| Biotin | 0.01% |
| *Camellia Sinensis* (White Tea) Leaf Extract | 0.01% |
| *Aesculus Hippocastanum* (Horse Chestnut) Seed Extract | 0.01% |
| *Cinnamomum Zeylanicum* (Cinnamon) Bark Extract | 0.01% |
| Butylene Glycol (and) *Saccharomyces*/Copper Ferment | 0.01% |
| Sodium Phosphate, Dibasic | 0.01% |
| Sodium Chloride, 25% soln. | 0.07% |
| Triethanolamine, 99% | 0.60% |
| Vitamin B-12 (0.10% soln.) | 0.05% |
| Folic Acid | 0.001% |

Myristoyl Tetrapeptide-12 has the amino acid sequence SEQ ID NO:2 Myr-KAKA-amine, with a chemical formula $C_{32}H_{63}N_7O_5$ and a molecular weight of 625.90. Myristol Pentapeptide-17 has the amino acid sequence SEQ ID NO:1 Myr-KLAKK-amide, with a chemical formula of C41H81N9O6, and a molecular weight of 796.16. The blend is 80% of Myristoyl pentapeptide-17 and 20% Myristoyl tetrapeptide-12. The peptides are provided at 0.5 mg/ml.

In some embodiments a cosmetic preparation for use on eyelashes has a formulation as follows:

| Marini Lash | | | |
|---|---|---|---|
| MATERIAL NAME | Current % (w/w) | Minimum % (w/w) | Maximum % (w/w) |
| DEIONIZED WATER | q.s To 100% | 98.3509 | 73.88 |
| SODIUM HYALURONATE (and) HYDROLYZED GLYCOSAMINO GLYCANS | 3.00 | 0.05 | 10.00 |
| PROPYLENE GLYCOL (and) DIAZOLIDYNYL UREA (and) METHYLPARABEN (and) PROPYLPARABEN | 1.00 | 0.50 | 1.50 |
| C12-C15 ALKYL BENZOATE | 0.50 | 0.01 | 3.00 |
| PANTHENOL | 0.50 | 0.01 | 3.00 |
| ACRYLATES/C10-C30 ALKYL ACRYLATES CROSSPOLYMER | 0.44 | 0.01 | 3.00 |
| MYRISTOYL PENTAPEPTIDE-17 and/or MYRISTOYL TETRAPEPTIDE-12 at 500 ppm | 0.20 | 0.01 | 0.50 |
| LINOLEIC ACID (and) LINOLENIC ACID (and) TOCOPHEROL | 0.10 | 0.001 | 2.00 |
| BIOTIN | 0.01 | 0.001 | 2.00 |
| *CAMELLIA SINENSIS* (WHITE TEA) LEAF EXTRACT | 0.01 | 0.001 | 2.00 |
| *AESCULUS HIPPOCASTANUM* (HORSE CHESTNUT) SEED EXTRACT | 0.01 | 0.001 | 0.50 |
| *CINNAMOMUM ZEYLANICUM* (CINNAMON) BARK EXTRACT | 0.01 | 0.001 | 0.50 |
| BUYTLENE GLYCOL (and) *SACCHAROMYCES*/COPPER FERMENT | 0.01 | 0.001 | 0.50 |
| SODIUM PHOSPHATE, DIBASIC | 0.01 | 0.001 | 0.10 |
| SODIUM CHLORIDE, 25% | 0.07 | 0.001 | 0.10 |
| TRIETHANOLAMINE, 99% | 0.60 | 0.10 | 2.00 |
| VITAMIN B12 (0.1% SOLUTION) | 0.05 | 0.001 | 1.00 |
| FOLIC ACID | 0.001 | 0.0001 | 0.05 |
| TOTAL = | 100.00% | | |

| HYDRO-GEL I | |
|---|---|
| ingredient | % w/w |
| DI Water | 71-82 |
| Myristoyl Pentapeptide-17 and/or Myristoyl Tetrapeptide-12 (500 ppm) | 0.2% |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Methylparaben | 0.30 |
| Polysorbate 20 | 0.25 |
| Disodium EDTA | 0.10 |
| Germall II | 0.10 |
| Total | 100.00 |

| HYDRO-GEL | |
|---|---|
| ingredient | % w/w |
| DI Water | 71-82 |
| Myristoyl Pentapeptide-17 (and) Myristoyl Tetrapeptide-12 (500 ppm) | 0.2% |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Methylparaben | 0.30 |
| Polysorbate 20 | 0.25 |
| Disodium EDTA | 0.10 |
| Germall II | 0.10 |
| Total | 100.00 |

| HYDRO-GEL II | |
|---|---|
| ingredient | % w/w |
| DI Water | 71-82 |
| Myristoyl Pentapeptide-17 (and) Myristoyl Tetrapeptide-12 (500 ppm) | 0.2% |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Methylparaben | 0.30 |
| Polysorbate 20 | 0.25 |
| Disodium EDTA | 0.10 |
| Germall II | 0.10 |
| Total | 100.00 |

| ANHYDROUS SERUM | |
|---|---|
| ingredient | % w/w |
| Myristoyl Pentapeptide-17 (and) Myristoyl Tetrapeptide-12 (500 ppm) | 0.2% |
| Cyclomethicone | 62-72 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total | 100.00 |

| OIL-IN-WATER EMULSION | |
|---|---|
| Ingredient | % w/w |
| DI Water | 65-75 |
| Myristoyl Pentapeptide-17 (and) Myristoyl Tetrapeptide-12 (500 ppm) | 0.2% |
| Carbomer | 0.30 |
| Disodium EDTA | 0.10 |
| Glycerin | 3.00 |
| Polysorbate 20 or 80 | 2.50 |
| Propylene or Butylene Glycol | 2.00 |
| Methylparaben | 0.30 |
| Triethanolamine 99% | 0.30 |
| Isopropyl Myristate | 5.00 |
| Octyl Palmitate | 3.00 |
| Cetyl Alcohol | 1.00 |
| Dimethicone 100 cst | 0.50 |
| Beeswax | 0.30 |
| Propylparaben | 0.10 |
| Germall II | 0.10 |
| Fragrance | 0.10 |
| Active Agent (e.g., Bimatoprost) | 0.1 to 10% |
| Total | 100.00 |

| WATER-IN-OIL EMULSION | |
|---|---|
| ingredient | % w/w |
| DI Water | 55-65 |
| Myristoyl Pentapeptide-17 (and) Myristoyl Tetrapeptide-12 (500 ppm) | 0.2% |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Isopropyl Myristate | 5.00 |
| Octyl Palmitate | 3.00 |
| Dimethicone Copolyol | 2.50 |
| Dimethicone 100 cst | 0.50 |
| Beeswax | 0.30 |
| Propylparaben | 0.10 |
| Germall II | 0.10 |
| Fragrance | 0.10 |
| Total | 100.00 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for enhancing the appearance of eyelashes and/or eyebrows, the method comprising:
applying to a region of skin comprising hair follicles of the eyelashes and/or eyebrows a cosmetic formulation comprising:
at least one of an acylated five amino acid peptide having the amino acid sequence SEQ ID NO:1 Ac-KLAKK and an acylated four amino acid peptide having the amino acid sequence SEQ ID NO:2 Ac-KAKA at a concentration of from about 0.001 µg/ml to about 1 µg/ml;
a skin penetration enhancing agent;
herbal extracts of *Cinnamomum zeylanicum* bark extract, *Aesculus hippocastanum* seed extract, and *Camellia sinensis* leaf extract; and
a cosmetically acceptable vehicle in the pH range of about pH 3 to about pH 8;
wherein the appearance of said eyelashes and/or eyebrows is enhanced.

* * * * *